US00PP18496P3

(12) United States Plant Patent
Parham

(10) Patent No.: US PP18,496 P3
(45) Date of Patent: Feb. 19, 2008

(54) ***CHRYSANTHEMUM* PLANT NAMED 'RADIANT TIME'**

(50) Latin Name: *Chrysanthemum morifolium*
Varietal Denomination: Radiant Time

(75) Inventor: Ruth Parham, Bognor Regis (GB)

(73) Assignee: Cleangro Ltd., Chichester, West Sussex (GB)

( * ) Notice: Subject to any disclaimer, the term of this patent is extended or adjusted under 35 U.S.C. 154(b) by 0 days.

(21) Appl. No.: 11/490,443

(22) Filed: Jul. 20, 2006

(65) Prior Publication Data

US 2007/0033685 P1 Feb. 8, 2007

Related U.S. Application Data

(60) Provisional application No. 60/703,344, filed on Jul. 28, 2005.

(51) Int. Cl.
*A01H 5/00* (2006.01)

(52) U.S. Cl. ..... Plt./286
(58) Field of Classification Search ..... Plt./266
See application file for complete search history.

(56) References Cited

U.S. PATENT DOCUMENTS

PP14,896 P3 6/2004 Boeder ..... Plt./298

2003/0056261 P1 3/2003 Boeder ..... Plt./286

OTHER PUBLICATIONS

2003 Cleangro Brochure listing the Chrysanthemum varieties 'Doing Time', and 'Machismo Time'. See the photographs at pp. 8 and 9, respectively. Brochure was published Sep. 17, 2003.

2004 Cleangro Brochure listing the Chrysanthemum varieties 'Doing Time', 'Machismo Time' and 'Swing Time Dark'. See the photographs at pp. 9 and 10, respectively. Brochure was published Sep. 1, 2003.

2005 Cleangro Brochure listing the Chrysanthemum varieties 'Machismo Time' and 'Swing Time Dark'. See the photographs at p. 11. Brochure was published Sep. 1, 2004.

2001 Ficor Catalogue listing the Chrysanthemum varieties 'Doing Time' and 'Machismo Time' at pp. 4 and 9. Catalogue was published Oct. 12, 2000.

2004 Ficor Catalogue listing the Chrysanthemum varieties 'Doing Time', 'Machismo Time' and 'Swing Time Dark', at pp. 2–3, and pp. 6 and 7. Catalogue was published Oct. 1, 2003.

*Primary Examiner*—Kent Bell
*Assistant Examiner*—Annette H Para
(74) *Attorney, Agent, or Firm*—Winston & Strawn, LLP

(57) ABSTRACT

A new variety of *Chrysanthemum* plant named 'Radiant Time', having medium sized yellow and red blooms and a light green disc. The variety has a strong medium vigor with good foliage presentation and a long shelflife.

1 Drawing Sheet

Latin name of the genus and species: Botanical classification: *Chrysanthemum morifolium.*

Variety denomination: The new *Chrysanthemum* variety denomination is 'Radiant Time'.

BACKGROUND OF THE INVENTION

The present invention comprises a new and distinct cultivar of *Chrysanthemum* botanically known as *Chrysanthemum morifolium,* and referred to by the cultivar name 'Radiant Time'.

'Radiant Time', identified as 21589-0 originated from a cross made in a controlled breeding program in Chichester, West Sussex, United Kingdom.

The female parent of the new variety is Machismo Time (U.S. Plant Patent Application Publication No. 2003/0056261), identified as 20360-0. The male parent is the variety known as Swing Time Dark, (U.S. Plant Pat. No. 14,896). The new variety 'Radiant Time' has been asexually reproduced by vegetative cuttings, in Chichester, West Sussex, United Kingdom and the distinguishing characteristics are retained through successive generations of asexual reproduction.

BRIEF SUMMARY OF THE INVENTION

'Radiant Time' is a pot type of *Chrysanthemum* plant variety having medium sized blooms with yellow and red ray florets and yellow-green disc.

Comparison with Female Parent

Plants of the new *Chrysanthemum* variety 'Radiant Time' are dissimilar to the female parent 'Machismo Time' in plant habit and growth rate. In side-by-side comparisons in Chichester, West Sussex, United Kingdom, under commercial practice, plants of the new *Chrysanthemum* variety 'Radiant Time' differed from plants of the female parent 'Machismo Time' in the following characteristics:

1. The new variety 'Radiant Time' produces medium large yellow and red single flowers whereas the female parent 'Machismo Time' produces medium small yellow and red single flowers.
2. Plants of the new variety 'Radiant Time' have larger and taller inflorescence than plants of the female parent 'Machismo Time'.
3. Plants of the new variety 'Radiant Time' have a quicker response time than the plants of 'Machismo Time'.

4. Plants of the new variety 'Radiant Time' have a medium vigor whereas plants of 'Machismo Time' have a taller vigor.

Comparison with Male Parent

Plants of the new *Chrysanthemum* variety 'Radiant Time' are dissimilar to the male parent 'Swing Time Dark' in plant habit and growth rate. In side-by-side comparisons in Chichester, West Sussex, United Kingdom, under commercial practice, plants of the new *Chrysanthemum* variety 'Radiant Time' differed from plants of the male parent 'Swing Time Dark' in the following characteristics:

1. The new variety 'Radiant Time' produces yellow and red single flowers whereas the male parent 'Swing Time Dark' produces orange single flowers.
2. Plants of the new variety 'Radiant Time' have larger and taller inflorescence than plants of the male parent 'Swing Time Dark'.

Comparison with 'Doing Time'

Plants of the new *Chrysanthemum* variety 'Radiant Time' are similar to plants of the unpatented variety 'Doing Time' in plant habit and growth rate. However, in side-by-side comparisons in Chichester, West Sussex, United Kingdom, under commercial practice, plants of the new *Chrysanthemum* variety 'Radiant Time' compared to plants of 'Doing Time' in the following characteristics:

1. The new variety 'Radiant Time' produces flatter form of yellow and red single flowers whereas 'Doing Time' produces cupped yellow and red single flowers.
2. Plants of the new variety 'Radiant Time' have larger and taller inflorescence than plants of 'Doing Time'.
3. Plants of the new variety 'Radiant Time' have a longer shelflife than plants of 'Doing Time'.

BRIEF DESCRIPTION OF ILLUSTRATIONS

Typical specimens of the plant and flowers for the new *Chrysanthemum* variety 'Radiant Time' are shown in the accompanying digital photograph. The colors shown are as true as possible within the usual limits of this kind of illustration.

FIG. 1 is a whole plant view of the new variety 'Radiant Time' grown in a pot. The plant shown in the illustration and described below is 56 days from the onset of Short Days.

DETAILED BOTANICAL DESCRIPTION

The following description of the new *Chrysanthemum* variety 'Radiant Time' is of plants grown in a greenhouse in Chichester, West Sussex, United Kingdom, in the month of October. The cultivar has not been observed under all possible environmental conditions. The phenotype may vary significantly with variations in the environment such as temperature, length of day and light intensity, without any variance in genotype. The commercial classification of the new variety is a pot *Chrysanthemum.*

Plants of the new variety have been grown successfully under temperature conditions averaging about 19° C. at night and about 17° C. to 24° C. during the day under light conditions of about 2,500 Lux. The plants respond well to the use of growth retardant, such as one B9 treatment at about 2 grams per liter. To produce a commercial product, the plants may be pinched once with the center bud removed. The typical container size for commercial growth is 1 liter. It has been observed that the shelf life of the new variety is about 28 days with a response time of about 7 weeks. The new variety is suitable for growth in a temperature range of 15° C. to 25° C.

The following description is with respect to a plant produced as pot *Chrysanthemum.* In the description of this new *Chrysanthemum* variety, color values have been taken from The Royal Horticultural Society Colour Chart (R.H.S.C.C.).

Plant

Plant type: Pot.
Habit: Upright and free branching.
Height (cm): 17.
Width (cm): 26.
Stem:
*Length* (*cm*).—4.5.
*Diameter* (*cm*).—0.6.
*Texture.*—Slightly pubescent.
*Color.*—139C.
Branching characteristics: Upright and free branching.
Lateral branches:
*Length* (*cm*).—9.
*Diameter* (*cm*).—0.4.
*Texture.*—Slightly pubescent.
Number of breaks from pinch: 6.
Response time: 48 days.
Vigor: Medium.
Shelf life: 28 days.
Life of blooms: 28 days.
Disease (susceptibility/resistance observed): None observed to date.
Pest (susceptibility/resistance observed): None observed to date.
Drought and temperature (susceptibility/resistance observed): None observed to date.
Growth retardant type and treatment: 3 applications of 2.5 gm/liter B9 @ 2, 21 and 28 days after sticking unrooted cuttings.
The plants were grown for two weeks in Long Day conditions (20 hours of light) and then transferred to Short Day conditions (13 hours of dark).
Propagation:
*Type.*—Vegetative propagation via stem cuttings.
*Time to rooting.*—14 days with soil temperatures of 18° C.
*Rooting habit.*—After 7 Long Days, the first roots emerge and form root primordia. In 14 Long Days, a complete root system is developed.

Foliage

Number of leaves per lateral branch: 8.
Compound or single: Single.
Arrangement of leaves: Alternate.
*Shape of leaf.*—Typically 5 lobed.
*Size of leaf.*—Width (cm): 5.8 Length (cm): 8.5.
*Leaf apex.*—Acute.
*Base.*—Obtuse.
*Attachment.*—Petioled.
*Aspect.*—Slightly undulating.
*Margin.*—Palmately lobed.
*Surface characteristics.*—Top: Slightly pubescent. Bottom: Pubescent.
Petiole:
*Color.*—137B.
*Length* (*cm*).—1.5.
*Diameter* (*cm*).—0.4.
*Surface.*—Slightly pubescent.

Venation: Net, prominent lateral and mid-veins at underside.
*Color.*—Upper side: 138B. Under side: 138B.
Color:
*Mature leaf, upper side.*—137B; under side: 138B.
*Young leaf, upper side.*—137B; under side: 138B.

Flower

Flower appearance: Matte.
Flower type: Single.
Flower form: Flat form.
Flower shape: Circular.
Flowering habit: Cyme.
Number of blossoms per branch: 5.
Typical and observed flowering season: January to December.
Inflorescence form: Cyme.
*Depth of fully expanded blossoms* (*cm*).—1.
*Diameter of fully expanded blossoms* (*cm*).—7.5.
Phyllaries:
*Number.*—35.
*Color.*—137D.
*Length* (*cm*).—0.7.
*Width* (*cm*).—0.2.
*Texture/appearance.*—Slightly pubescent.
Peduncle:
*Length* (*cm*).—10.
*Diameter* (*cm*).—0.3.
*Angle from stem* (*degrees*).—10.
*Color.*—137D.
*Surface.*—Slightly pubescent.
*Habit.*—Slightly undulating.
*Strength.*—Strong.
Pedicel:
*Length.*—Terminal (cm): 4; lateral (cm): 3.5.
*Diameter* (*cm*).—0.2.
*Color.*—139C.
*Surface.*—Slightly pubescent.
*Habit.*—Straight.
*Strength.*—Strong.
Ray florets:
*Form/shape.*—Straight with parallel edges to the central mid vein.
*Texture/appearance.*—Matte.
*Number per flower.*—33.
*Length* (*cm*).—3; Width (cm): 7.
*Apex.*—Rounded.
*Base.*—Tapered.
*Margin.*—Entire.
Disc florets:
*Form/shape.*—Cylindric.
*Texture/appearance.*—Shiny.
*Number per flower.*—200.
*Length* (*cm*).—0.6; Width (cm): 0.1.
*Diameter of disc* (*cm*).—1.
Fragrance: None.
Flower bud (at onset of color):
*Length* (*cm*).—1.3.
*Diameter* (*cm*).—1.
*Form/shape.*—Globular.
General flower color:
1. *Ray florets, upper side.*—Immature: 33A from the center towards the base and 9A towards the apex. Mature: 33A from the center towards the base and 9A towards the apex. Older/Fading: 33B from the center towards the base and 9B towards the apex.
2. *Ray florets, under side.*—Immature: 34B from the center towards the base and 6A towards the apex. Mature: 34C from the center towards the base and 6A towards the apex. Older/Fading: 34C from the center towards the base and 6A towards the apex.
3. *Disc florets.*—Immature: 151A. Mature: 13B. Older/Fading: 13B.
4. *Bud.*—6A from center to apex and 34B from centre to base.

Flower progression with age: There is no change in the flower form but there is a slight color fading with age.

Reproductive Organs

Gynoecium present on ray and disc florets.
Ray florets per individual flower: Pistillate.
*Pistil number.*—35.
*Stigma color.*—154A.
*Stigma shape.*—Forked.
*Style color.*—154B.
*Style length* (*cm*).—0.3.
Disc florets per individual flower: Pistillate.
*Pistil number.*—200.
*Stigma color.*—154A.
*Stigma shape.*—Forked.
*Style color.*—154B.
*Style length* (*cm*).—0.3.
Androecium: Not observed.
Fruit and seeds: None observed.

What is claimed is:

1. A new and distinct variety of *Chrysanthemum* plant, substantially as described and illustrated herein.

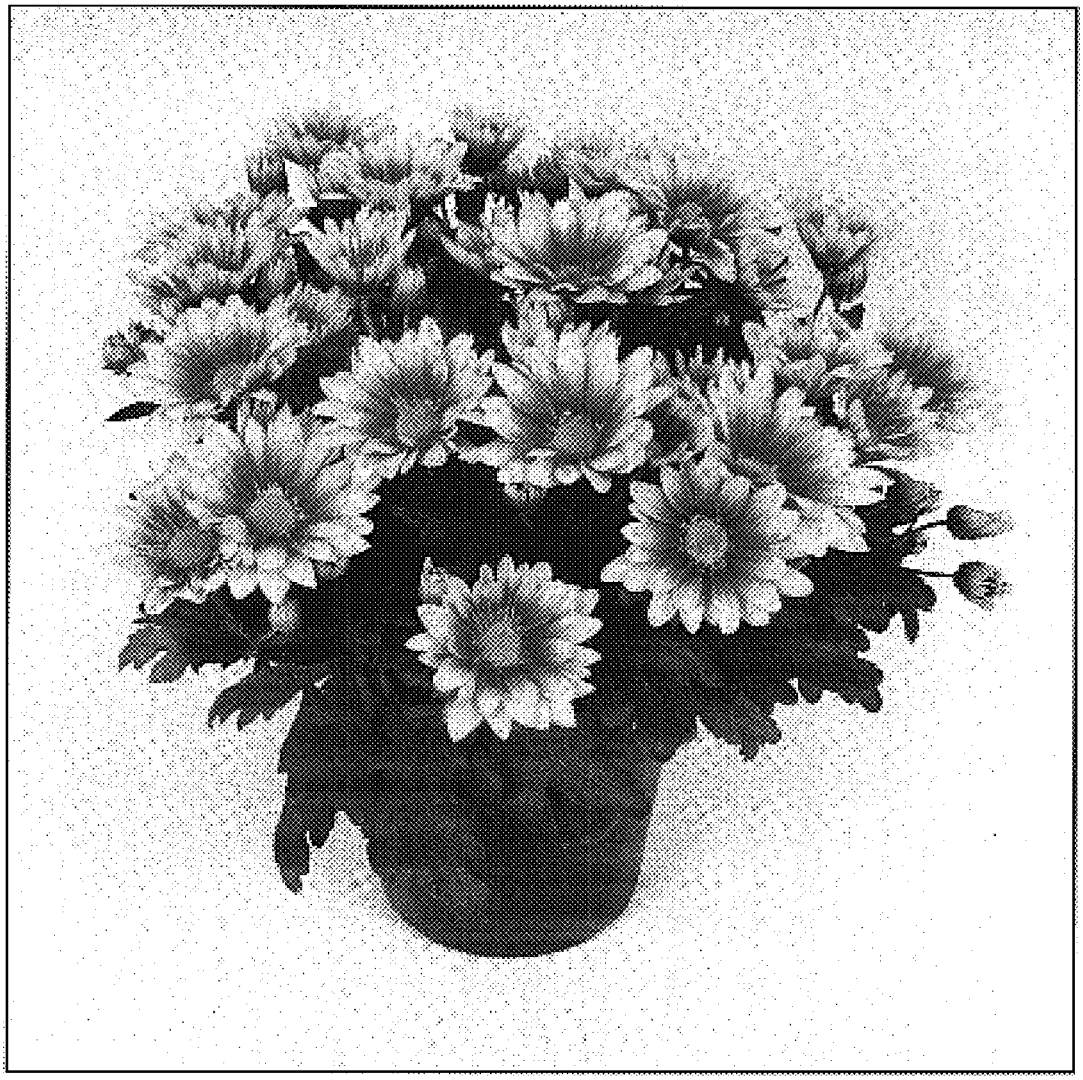

* * * * *